(12) United States Patent
Dai et al.

(10) Patent No.: US 6,569,893 B2
(45) Date of Patent: May 27, 2003

(54) AMINO ACID DERIVATIVES OF TRIPTOLIDE COMPOUNDS AS IMMUNE MODULATORS AND ANTICANCER AGENTS

(75) Inventors: Dongcheng Dai, Mountain View, CA (US); John M. Fidler, Oakland, CA (US); John H. Musser, San Carlos, CA (US)

(73) Assignee: Pharmagenesis, Inc., Palo Alto, CA (US)

( * ) Notice: Subject to any disclaimer, the term of this patent is extended or adjusted under 35 U.S.C. 154(b) by 0 days.

(21) Appl. No.: 10/098,009

(22) Filed: Mar. 14, 2002

(65) Prior Publication Data

US 2002/0193419 A1 Dec. 19, 2002

Related U.S. Application Data

(60) Provisional application No. 60/276,617, filed on Mar. 15, 2001.

(51) Int. Cl.$^7$ .................. A61K 31/343; C07D 407/14
(52) U.S. Cl. ............................ 514/468; 549/297
(58) Field of Search ................ 549/297; 514/468

(56) References Cited

U.S. PATENT DOCUMENTS

| | | | |
|---|---|---|---|
| 4,005,108 A | 1/1977 | Kupchan et al. | |
| 5,962,516 A | 10/1999 | Qi et al. | |
| 5,972,998 A | 10/1999 | Jung et al. | |
| 6,004,999 A | 12/1999 | Jung et al. | |
| 6,150,539 A | 11/2000 | Musser | |
| 6,294,546 B1 | 9/2001 | Rosen et al. | |
| 6,329,148 B1 | 12/2001 | Rosen et al. | |

FOREIGN PATENT DOCUMENTS

WO WO 00/63212 10/2000

OTHER PUBLICATIONS

Van Tamelen et al (1982): STN International, CAPLUS database (Columbus, Ohio), No. 96:143107.*

* cited by examiner

Primary Examiner—Alan L. Rotman
Assistant Examiner—Golam M. M. Shameem
(74) Attorney, Agent, or Firm—LeeAnn Gorthey; Perkins Coie LLP

(57) ABSTRACT

Compounds which are prodrugs of triptolide or its derivatives, containing an amino acid or oligopeptide moiety, are used for anticancer or immunosuppressive treatment. The compounds are of the structure:

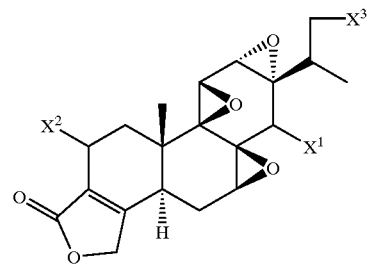

where $X^1$ is OH or $OR^1$, and $X^2$ and $X^3$ are independently OH, $OR^1$ or H, with the proviso that at least one of $X^1$, $X^2$ and $X^3$ is $OR^1$, and at least one of $X^2$ and $X^3$ is H; and $R^1$, is selected from the group consisting of:

$$C(=O)CH—(CH_2)_3—NP^1 \quad\quad (a)$$

$$C(=O)CHY—NHP^1 \quad\quad (b):$$

$$C(=O)CH(NHP^1)—(CH_2)_m—C(=O)OP^2 \quad\quad (c):$$

$$C(=O)(CH_2)_n—CH(NHP^1)—C(=O)OP^2 \text{ and} \quad\quad (d):$$

$$[C(=O)CHY—NH]_z—C(=O)CHY—NHP^1; \quad\quad (e):$$

where Y is a side chain of a naturally occurring amino acid or a one- or two-carbon homolog thereof; $P^1$ is selected from the group consisting of H, $C(=O)OR^2$, and $C(=O)R^3$, where each of $R^2$ and $R^3$ is independently H, alkyl, alkenyl, aryl, or aralkyl; m is an integer from 0–5; n is an integer from 0–5; z is an integer from 2–10; and $P^2$ is selected from the group consisting of H, alkyl, alkenyl, aryl, and aralkyl.

15 Claims, No Drawings

AMINO ACID DERIVATIVES OF TRIPTOLIDE COMPOUNDS AS IMMUNE MODULATORS AND ANTICANCER AGENTS

This application claims priority to U.S. Provisional Application Ser. No. 60/276,617, filed Mar. 15, 2001, which is hereby incorporated by reference in its entirety.

FIELD OF THE INVENTION

The present invention relates to immunomodulation or anticancer treatment using compounds which are prodrugs of triptolide or its derivatives.

REFERENCES

Gleichmann, E. et al., *Immunol. Today* 5:324 (1984).
Kocienski, P. J., *PROTECTING GROUPS*, Georg Thieme Verlag, Stuttgart (1994).
Korngold, R. and Sprent, J., *J. Exp. Med.* 148:1687 (1978).
Kupchan, S. M. et al., *J. Am. Chem. Soc.* 94:7194 (1972).
Kupchan, S. M. et al., U.S. Pat. No. 4,005,108 (1977).
Lipsky et al., U.S. Pat. No. 5,294,443 (1994).
Ma et al., *J. Chin. Pharm. Sci.* 1:12 (1992).
Murase, N. et al., *Transplantation* 55:701 (1993).
Ono and Lindsey, *J. Thor. Cardiovasc. Surg.* 57(2):225–29 (1969).
Pu, L. et al., *Zhongguo Yaoli Xuebao* 11:76 (1990).
Wang, J. and Morris, R. E., *Transplantation Proc.* 23:699 (1991).
Zheng et al., *Zhongguo Yixue Kexueyuan Xuebao* 13:391 (1991).
Zheng et al., *Zhongguo Yixue Kexueyuan Xuebao* 16:24 (1994).

BACKGROUND OF THE INVENTION

A number of compounds derived from the Chinese medicinal plant *Tripterygium wilfordii* (TW) have been identified as having immunosuppressive activity, e.g. in the treatment of autoimmune disease, and in treating or preventing transplantation rejection, including the treatment of graft-versus-host disease (GVHD), a condition in which transplanted marrow cells attack the recipient's cells. See, for example, co-owned U.S. Pat. No. 6,150,539 (Triptolide prodrugs having high aqueous solubility), U.S. Pat. No. 5,962,516 (Immunosuppressive compounds and methods), U.S. Pat. No. 5,843,452 (Immunotherapy composition and method), U.S. Pat. No. 5,759,550 (Method for suppressing xenograft rejection), U.S. Pat. No. 5,663,335 (Immunosuppressive compounds and methods), and U.S. Pat. No. 5,648,376 (Immunosuppressant diterpene compound), and references cited therein. Such compounds have also been reported to show anticancer activity. See, for example, Kupchan et al., 1972, 1977, as well as copending and co-owned U.S. application Ser. No. 09/766,156.

Triptolide, 16-hydroxy triptolide, triptophenolide, tripdiolide, and celastrol are representative compounds isolated from TW (see e.g. Lipsky et al., 1994; Zheng et al., 1991, 1994; Ma et al., 1992). However, the low water solubility of these compounds has limited their ready administration and therapeutic effectiveness. It would be desirable to have immunosuppressive compounds with improved water solubility and low toxicity. In addition, it would be desirable for such compounds to exhibit immunosuppressive activity in their water-soluble form, or to be convertible to an immunosuppressive form by metabolic processes in vivo.

It would also be desirable to have as part of the xenobiotic compound moieties that are naturally sensitive to metabolic processes. The inclusion of an L-amino acid moiety in the structure of the prodrug is expected to render it more susceptible to certain types of metabolic processes, thereby releasing an active moiety with altered and more rapid kinetics.

Conversely, in some applications it would be desirable to have as part of the xenobiotic compound moieties that are naturally resistant to metabolic processes. The inclusion of a D-amino acid moiety in the structure of the prodrug may render it more resistant to certain types of metabolic processes, thereby releasing an active moiety with altered and possibly slower kinetics.

The inclusion of an amino acid moiety in the structure of the prodrug may also alter absorption into the body when administered by a route other than intravenously. The amino acid moiety may also alter the biodistribution of the agent, giving it better access to organs, tissues, tumors, or areas of the body where therapy is useful or desired, or better access to cells, their outer membranes or cell interiors. The amino acid moiety may also alter the excretion of the prodrug, thereby altering the level in the body and the biodistribution, and/or alter bioavailability, by altering binding to blood components (such as albumin) or other tissues.

The inclusion of multiple amino acid moieties as an oligopeptide may be used to target the prodrug to cancer or immune regulatory cells. Targeted prodrugs that bind to specific molecular sites near, on, or in cancer cells, or are selectively transported within these cells, have the potential to significantly decrease side effects associated with anti-tumor drug administration. In addition, prodrugs that are selectively converted by tumor-specific enzymes (as determined e.g. by screening extent of conversion by preparations of such enzymes) can also reduce such side effects, in that they are converted to their active form only in the proximity of the tumor target.

Likewise, targeted prodrugs that bind to immune regulatory cells, such as T-cells, B-cells or lymphocytes, or are selectively transported into these cells, have the potential to significantly decrease side effects associated with immunosuppressant drug administration. Thus, conjugation of olipeptides to triptolide or triptolide related molecules may result in enhanced drug localization, showing an improved efficacy and toxicity profile compared to that of the triptolide alone.

SUMMARY OF THE INVENTION

The present invention includes, in one aspect, a compound having the structure:

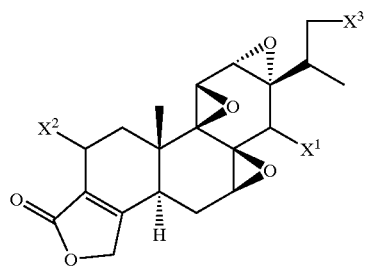

where
$X^1$ is OH or $OR^1$, and $X^2$ and $X^3$ are independently OH, $OR^1$ or H, with the proviso that at least one of $X^1$, $X^2$ and $X^3$ is $OR^1$, and at least one of $X^2$ and $X^3$ is H; and $R^1$ is selected from the group consisting of:

(a) $C(=O)CH\text{——}(CH_2)_3\text{——}NP^1$ (cyclic, connecting CH to N)

(b): $C(=O)CHY\text{——}NHP^1$ (c)

NHP¹  O
   \\  /
    structure with $(\ )_m$ and $OP^2$, with =O on left side (d)

O   NHP¹
 \\\\ /
  structure with $(\ )_n$ and $OP^2$, with =O on right and (e): $[C(=O)CHY\text{——}NH]_z\text{——}C(=O)CHY\text{——}NHP^1$;

where:

Y is a side chain of a naturally occurring amino acid or a one- or two-carbon homolog thereof;

$P^1$ is selected from the group consisting of H, $C(=O)OR^2$, and $C(=O)R^3$, wherein each of $R^2$ and $R^3$ is independently H, alkyl, alkenyl, aryl, or aralkyl;

m is an integer from 0–5;

n is an integer from 0–5; and z is an integer from 2–10.

$P^2$ is selected from the group consisting of H, alkyl, alkenyl, aryl, and aralkyl.

In one embodiment, $P^1$ and $P^2$ are non-hydrogen. In further embodiments of this category, $R^2$ and $R^3$ are also non-hydrogen; i.e. selected from alkyl, alkenyl, aryl, and aralkyl.

In selected embodiments, "alkyl" and "alkenyl" are lower alkyl and alkenyl, containing one to six carbon atoms; in other embodiments, "alkyl" and "alkenyl" are fatty alkyl and alkenyl, containing about 10 to 24, preferably about 12 to 18, carbon atoms.

The chiral α-carbon bearing the nitrogen atom, in each of groups (a)–(d), is of the L (naturally occurring) configuration, the D configuration, or a mixture thereof. In selected embodiments, this carbon is of the L configuration. In other embodiments, this carbon is of the D configuration.

In preferred embodiments, Y is a side chain of a naturally occurring amino acid.

In selected embodiments, $X^2=X^3=H$. In further embodiments of this class, $R^1$ is selected from (c)

NHP¹  O
   \\  /
    structure with $(\ )_m$ and $OP^2$ and (d)

O   NHP¹
 \\\\ /
  structure with $(\ )_n$ and $OP^2$, where $P^1$ is preferably $C(=O)R^3$.

In other aspects, the invention provides methods of anticancer treatment and of effecting immunosuppression. In accordance with these methods, a compound in accordance with claim 1, or a pharmaceutically acceptable salt thereof, is administered to a subject in need of such treatment. In selected embodiments, the anticancer treatment is treatment of colon cancer, breast cancer, lung cancer, or prostate cancer. Immunosuppressive treatments include inhibition of transplant rejection, inhibition of graft-versus-host disease, and treatment of autoimmune disease, such as rheumatoid arthritis.

These and other objects and features of the invention will become more fully apparent when the following detailed description of the invention is read in conjunction with the accompanying drawings.

DETAILED DESCRIPTION OF THE INVENTION

I. Definitions

The terms below have the following meanings unless indicated otherwise.

A "naturally occurring amino acid" is one of the following, referred to by full name or by standard single-letter or three-letter notation: A, Ala, alanine; C, Cys, cysteine; D, Asp, aspartic acid; E, Glu, glutamic acid; F, Phe, phenylalanine; G, Gly, glycine; H, His, histidine; I, Ile, isoleucine; K, Lys, lysine; L, Leu, leucine; M, Met, methionine; N, Asn, asparagine; P, Pro, proline; Q, Gln, glutamine; R, Arg, arginine; S, Ser, serine; T, Thr, threonine; V, Val, valine; W, Trp, tryptophan; X, Hyp, hydroxyproline; and Y, Tyr, tyrosine. Naturally occurring amino acids are of the L configuration. However, a compound bearing "a side chain of a naturally occurring amino acid" need not be of a particular configuration.

Unless otherwise stated, the amino acid moieties utilized in the compounds of the present invention can be of either the L-(naturally occurring) or D-configuration or can be mixtures of the D- and L-isomers, including racemic mixtures.

"Alkyl" refers to a fully saturated acyclic monovalent radical containing carbon and hydrogen, which may be branched or a straight chain, typically having 1 to about 24 carbon atoms. Higher alkyl or "fatty" alkyl groups include those having about 10 to 24, in one embodiment 12 to 18, carbon atoms. "Lower alkyl" refers to an alkyl radical of 1 to 6 carbon atoms, as exemplified by methyl, ethyl, n-butyl, i-butyl, t-butyl, isoamyl, n-pentyl, and isopentyl.

"Alkenyl" refers to an unsaturated acyclic monovalent radical containing carbon and hydrogen, which may be branched or a straight chain. The alkenyl group may be monounsaturated or polyunsaturated.

"Aryl" refers to a substituted or unsubstituted monovalent aromatic radical, generally having a single ring (e.g., benzene) or two condensed rings (e.g., naphthyl). Monocyclic aryl groups are generally preferred. The term includes heteroaryl groups, which are aromatic ring groups having one or more nitrogen, oxygen, or sulfur atoms in the ring, such as furyl, pyrrole, pyridyl, and indole. By "substituted"

is meant that one or more ring hydrogens in the aryl group is replaced with a group or groups preferably selected from fluorine, chlorine, bromine, methyl, ethyl, hydroxy, hydroxymethyl, nitro, amino, methylamino, dimethylamino, methoxy, halomethoxy, and halomethyl.

"Aralkyl" refers to an alkyl, preferably lower ($C_1$–$C_4$, more preferably $C_1$–$C_2$) alkyl, substituent which is further substituted with an aryl group; examples are benzyl and phenethyl. Also included is fluorenylmethyl, a component of the widely employed Fmoc (fluorenylmethoxycarbonyl) protecting group.

The term 'oligopeptide' refers to combinations of 2 to 10 amino acids in peptide linkages.

The term "pharmaceutically acceptable salt" encompasses carboxylate salts having organic and inorganic cations, such as alkali and alkaline earth metal cations (for example, lithium, sodium, potassium, magnesium, barium and calcium); ammonium; or organic cations, for example, dibenzylammonium, benzylammonium, 2-hydroxyethylammonium, bis(2-hydroxyethyl) ammonium, phenylethylbenzylammonium, and the like. Other cations encompassed by the above term include the protonated form of procaine, quinine and N-methylgliicosamine, and the protonated forms of basic amino acids such as glycine, ornithine, histidine, phenylglycine, lysine, and arginine.

The term also includes salts formed by standard acid-base reactions with basic groups, such as amino groups, having a counterion derived from an organic or inorganic acid. Such counterions include chloride, sulfate, phosphate, acetate, succinate, citrate, lactate, maleate, fumarate, palmitate, cholate, glutamate, glutarate, tartrate, stearate, salicylate, methanesulfonate, benzenesulfonate, sorbate, picrate, benzoate, cinnamate, and the like.

For the purposes of the current disclosure, the following numbering scheme is used for triptolide and triptolide analogs:

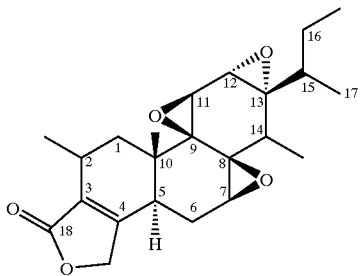

A "triptolide compound" can include triptolide (having a single hydroxyl group at C-14), tripdiolide (2-hydroxy triptolide), or 16-hydroxytriptolide.

II. Immunomodulating and Anticancer Agents

As noted above, triptolide compounds and various derivatives and prodrugs have been shown to have immunosuppressive activity in the treatment of autoimmune disease, and in treating or preventing transplantation rejection, including the treatment of graft-versus-host disease (GVHD), a condition in which transplanted marrow cells attack the recipient's cells. See, for example, co-owned U.S. Pat. No. 6,150,539 (Triptolide prodrugs having high aqueous solubility), U.S. Pat. No. 5,962,516 (Immunosuppressive compounds and methods), U.S. Pat. No. 5,843,452 (Immunotherapy composition and method), U.S. Pat. No. 5,759,550 (Method for suppressing xenograft rejection), U.S. Pat. No. 5,663,335 (Immunosuppressive compounds and methods), and U.S. Pat. No. 5,648,376 (Immunosuppressant diterpene compound), and references cited therein. Such compounds have also been reported to show anticancer activity. See, for example, Kupchan et al., 1972, 1977, as well as copending and co-owned U.S. application Ser. No. 09/766,156.

The low water solubility of the unmodified compounds, e.g. of unmodified triptolide, has limited their ready administration and therapeutic effectiveness. Accordingly, the authors have provided derivatives of these compounds having improved aqueous solubility as well as high therapeutic activity. See U.S. Pat. Nos. 6,150,539, 5,962,516, and 5,663,335, cited above. However, none of these disclosed amino acid- or oligopeptide-containing prodrugs.

Preferred amino acid- or oligopeptide-derivatized compositions of the invention have the structure I:

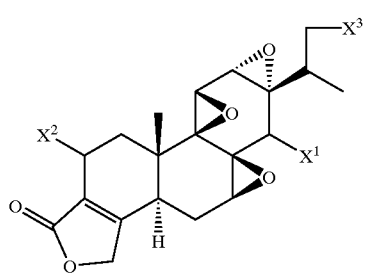

where
$X^1$ is OH or $OR^1$, and $X^2$ and $X^3$ are independently OH, $OR^1$, or H, with the proviso that at least one of $X^1$, $X^2$ and $X^3$ is $OR^1$, and at least one of $X^2$ and $X^3$ is H; and
$R^1$ is selected from the group consisting of:

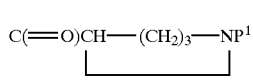 (a)

 (b):

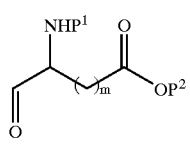 (c)

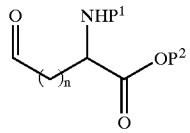 (d)

and

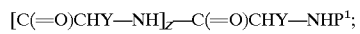 (e):

where:
Y is a side chain of a naturally occurring amino acid or a one- or two-carbon homolog thereof;
$P^1$ is selected from the group consisting of H, C(=O) $OR^2$, and C(=O)$R^3$, wherein each of $R^2$ and $R^3$ is independently H, alkyl, alkenyl, aryl, or aralkyl;
m is an integer from 0–5;
n is an integer from 0–5; and z is an integer from 2–10.

P² is selected from the group consisting of H, alkyl, alkenyl, aryl, and aralkyl.

In one embodiment, P¹ and P² are non-hydrogen. In further embodiments of this category, R² and R³ are also non-hydrogen; i.e. selected from alkyl, alkenyl, aryl, and aralkyl.

In selected embodiments, "alkyl" and "alkenyl" are lower alkyl and alkenyl, containing one to six carbon atoms; in other embodiments, "alkyl" and "alkenyl" are fatty alkyl and alkenyl, containing about 10 to 24, preferably about 12 to 18, carbon atoms.

As noted above, "aryl" refers to a substituted or unsubstituted monovalent aromatic radical, generally having a single ring (e.g., benzene) or two condensed rings (e.g., naphthyl). Monocyclic aryl groups are generally preferred. The term includes heteroaryl groups, which are aromatic ring groups having one or more nitrogen, oxygen, or sulfur atoms in the ring, such as furyl, pyrrole, pyridyl, and indole. By "substituted" is meant that one or more ring hydrogens in the aryl group is replaced with a group or groups preferably selected from fluorine, chlorine, bromine, methyl, ethyl, hydroxy, hydroxymethyl, nitro, amino, methylamino, dimethylamino, methoxy, halomethoxy, and halomethyl. In selected embodiments, the aryl group (including aralkyl) is a hydrocarbon group which is unsubstituted or substituted a group or groups selected from fluorine, chlorine, bromine, methyl, ethyl, methoxy, halomethoxy, and halomethyl.

In each of groups (a)–(e), the chiral carbon(s) bearing the nitrogen atom(s) are of either the D- or the L-configuration, or may include a mixture of the two configurations, including a racemic mixture. In selected embodiments, the configuration is L; in other embodiments, the configuration is D.

Note that, in group (b), the "side chain" can be hydrogen, as in the amino acid glycine. In preferred embodiments of group (b), Y is a side chain of a naturally occurring amino acid. A "one- or two-carbon homolog thereof" is a side chain producing by adding or deleting one or two methylene (CH₂) moieties from a naturally occurring side chain. For example, such homologs of the alanine side chain (methyl) would be ethyl and propyl. Such homologs of the lysine side chain (4-aminobutyl) would include 3-aminopropyl, 5-aminopentyl, and 4-amino-3-methyl butyl. Of these homologs, one-carbon homologs are preferred.

In any of groups (a)–(e), the amine nitrogen (the terminal amine in group (e)) may bear a further carboxyl or acyl group (i.e. where P¹ is C(=O)OR² or C(=O)R³), thus forming a carbamate or an amide, respectively.

The compounds are derivatives of triptolide (having a single hydroxyl group at C-14), tripdiolide (2-hydroxy triptolide), or 16-hydroxytriptolide. In selected embodiments, the compounds are derivatives of triptolide, having a single hydroxyl group at C-14, i.e. where X²=X³=H.

In one embodiment, R¹ is defined by group (e) above. In further embodiments, R¹ is selected from groups (c) and (d) above. In a still further embodiment, R¹ is represented by group (c). In these embodiments, when P¹ is C(=O)OR² or C(=O)R³, R² and R² are preferably selected from alkyl and aralkyl.

The compound may be provided as a pharmaceutically acceptable salt; i.e. a protonated amine salt having an anionic counterion, a carboxylate salt having a cationic counterion, or a zwitterion.

The compounds possess greater water solubility and modified bioprocessing as compared to the non-derivatized starting compounds, and are useful as prodrugs for immunosuppressive, anti-inflammatory, and anticancer applications, as described further below.

Higher water solubility is particularly desirable for prodrugs administered intravenously, e.g. in anticancer treatment. Alternatively, in immunosuppressive treatment, particularly for chronic conditions, oral administration is generally preferred, and the prodrugs may be designed to have a higher degree of lipid solubility than those intended for intravenous administration. Such prodrugs preferably include non-hydrogen substituents for the variables P¹ and/or P² above.

III. Synthesis

Compounds in accordance with the present invention, as defined by Formula I above, may be prepared from triptolide, tripdiolide, or 16-hydroxytriptolide, which can be obtained from the root xylem of the Chinese medicinal plant *Tripterygium Wilfordii* (TW) or from other known sources. The TW plant is found in the Fujian Province and other southern provinces of China; TW plant material can generally be obtained in China or through commercial sources in the United States. Methods for preparing triptolide, tripdiolide, and 16-hydroxytriptolide are known in the art and are described, for example, in Kupchan et al. (1972); Kupchan et al. (1977); Lipsky et al. (1994); Pu et al. (1990); and Ma et al. (1992).

The derivatives of the invention are prepared, in general, by condensation of the hydroxylated triptolide parent compound material with the carboxylic acid functionality of an amino acid, or an activated derivative such as an acid chloride (R¹Cl) or anhydride (R¹OC(O)R, where R is lower alkyl, typically methyl). Reactions with the carboxylic acid are typically carried out in the presence of a coupling agent such as dicyclohexylcarbodiimide (DCC) and a catalytic amount of an acylation catalyst such as 4-(dimethylamino) pyridine (DMAP). Any free amino groups in the amino acid can be protected using any of a variety of well known protecting groups, such as tBOC or FMOC. Alternatively, for compounds such as shown in groups (c), group (d), or group (b) where P¹ is C(=O)OR² or C(=O)R³, the amine is reacted with a carboxylic acid (R³C(O)OH) or carbonate (R²OC(O)OH), or activated derivative thereof, to form the amide or carbamate derivative, respectively. Any other reactive groups, such as active amino acid side chains, are also protected, according to well known methods.

Compounds of group (c) and (d) can be prepared using α-amino diacid starting materials. In each case, a diacid, such as malonic, succinic, glutaric, adipic, heptanedioic, or octanedioic (m=0–5 in group (d)) having one α-amino group, which may be derivatized or protected, is used. N-protected cyclic anhydrides of such compounds, such as 2-formamido succinic anhydride or 2-acetamido glutaric anhydride, may also be used. Reaction of the hydroxylated starting material (i.e. the triptolide compound) with the carboxyl moiety adjacent to the amino (or protected amino) group produces compounds of group (c), while reaction with the carboxyl moiety more remote from the amino group produces compounds of group (d). When mixtures are produced, they may be separated if desired by standard methods such as chromatography.

Protected α-amino acids suitable for these reactions are frequently commercially available, or they can be prepared by known methods, including known methods of asymmetric synthesis, optical resolution, or chromatography on chiral supports, if necessary. The development of such methods has been an active field of research for many years and is the subject of many articles, books and treatises. The amino compounds may be readily converted to the amide or carbamate derivatives discussed above, if desired.

Compounds of group (e) can be prepared using oligopeptides which are derivatized or protected except for the C-terminal carboxyl group. Such oligopeptides can be synthesized by well known methods and are frequently commercially available. Reaction of the hydroxylated starting material (i.e. the triptolide compound) with the C-terminal carboxyl moiety of the oligopeptide produces compounds of group (e). When mixtures are produced, they may be separated if desired by standard methods such as chromatography.

The preparation of several C-14 triptolide derivatives in accordance with the invention is described in the Examples, below.

In cases where all available hydroxyl groups on the starting material are to be derivatized, an excess of the carboxylic acid or active derivative may be used to drive the reaction to completion. The compound 16-hydroxytriptolide contains two free hydroxyl groups, one secondary (at C-14) and one primary (at C-16). Since the hydroxyl group at the 16-position is more reactive than the 14-hydroxyl group for steric reasons, mono- and diester derivatives can be selectively made using appropriate reaction conditions. Reaction with a stoichiometric amount of a selected carboxylic acid yields the monoester derivatized at the 16-position, with the 14-hydroxyl group remaining free. Reaction with an excess of the carboxylic acid is effective to derivatize both hydroxyl groups, affording the diester.

Monoester derivatives substituted at the more hindered (secondary) hydroxyl group can be prepared by first selectively protecting the less hindered (primary) hydroxyl group, carrying out the condensation reaction with the selected carboxylic acid at the unprotected position, and then removing the protecting group. Suitable hydroxyl protecting groups are well known, and are described, for example, by Kocienski (1994).

Selective single derivatization of tripdiolide (2-hydroxytriptolide) is more difficult because of the similar reactivities of the two secondary hydroxyls. Accordingly, the 2- and 14-monoesters may be prepared as a mixture either by (1) reacting tripdiolide with a comparable amount of carboxylic acid (e.g., 1 to 3 equivalents) or (2) briefly reacting tripdiolide with excess carboxylic acid followed quickly by addition of excess alcohol (e.g., ethanol) to quench the excess carboxylic acid. In either case, a mixture of mono- and diester forms can be obtained which may then be separated by standard chromatographic methods such as HPLC.

Metal salts and amine salts of the amino and carboxyl ester compounds of the invention are readily prepared by reaction or exchange with an appropriate counterion.

IV. Prodrug Conversion in Serum

Several compounds of formula I were prepared, as described in the Examples. In preliminary assays, the compounds were evaluated for their capacity to induce apoptosis in cells from the Jurkat human T lymphocyte cell line, after incubation with pooled human serum for 48 hrs at 37° C. (see Example 7). One of the compounds was also analyzed for its capacity to inhibit IL-2 production in Jurkat human T lymphocyte cells (see Example 8). Controls consisted of the compounds incubated in complete tissue culture medium (RPMI 1640 medium plus 5% heat-inactivated fetal calf serum, 1% HEPES, 1% pen/strep, 1% glutamine) rather than human serum.

The results of the assays are presented in Table 1. The $ED_{50}/IC_{50}$ values (column 3) are calculated directly from the data in each experiment, and the % conversion values (column 4) are calculated as percent of the $ED_{50}$ or $IC_{50}$ value produced by triptolide, incubated in the same plasma (i.e. in the same experiment).

TABLE 1

Apoptosis/IL-2 inhibition assay analysis of prodrug conversion to bioactive drug

|  | Compound | ED50 (nM) after 48 hr incubation with human serum | Conversion (relative activity compared to PG490) (%) |
|---|---|---|---|
| TdT Apoptosis Assay | PG657 | 300 | 10 |
|  | PG658 | 750 | 4.0 |
|  | PG659 | 80 | 38 |
|  | PG660 | 1100 | 2.7 |
| Annexin Apoptosis Assay | PG661 | 34661 | 0.16 |
| IL-2 Inhibition Assay | PG661 | 330 (IC50) | 1.4 |

In these preliminary results, it can be noted that the compound in which the amino acid moiety had no amine or carboxyl substitution (that is, $P^1$ and $P^2$ are both hydrogen; compound PG661, as prepared in Example 6) was converted at a substantially lower rate than compounds with alkyl or aralkyl substitution at the amino acid nitrogen and carboxyl groups. While not wishing to be bound by theory, it is possible that these hydrocarbon regions promote substrate recognition of the compounds by esterases, such as phospholipase A2, which have binding regions both for the ester group and for the neighboring lipid component(s) of glycerol ester-based phospholipids.

V. Therapeutic Compositions

Formulations containing the triptolide analogs of the invention may take the form of solid, semi-solid, lyophilized powder, or liquid dosage forms, such as tablets, capsules, powders, sustained-release formulations, solutions, suspensions, emulsions, ointments, lotions, or aerosols, preferably in unit dosage forms suitable for simple administration of precise dosages. The compositions typically include a conventional pharmaceutical carrier or excipient and may additionally include other medicinal agents, carriers, or adjuvants. Preferably, the composition will be about 0.5% to 75% by weight of a compound or compounds of the invention, with the remainder consisting of suitable pharmaceutical excipients. For oral administration, such excipients include pharmaceutical grades of mannitol, lactose, starch, magnesium stearate, sodium saccharine, talcum, cellulose, glucose, gelatin, sucrose, magnesium carbonate, and the like. If desired, the composition may also contain minor amounts of non-toxic auxiliary substances such as wetting agents, emulsifying agents, or buffers.

The composition may be administered to a subject orally, transdermally or parenterally, e.g., by intravenous, subcutaneous, intraperitoneal, or intramuscular injection.

For use in oral liquid preparation, the composition may be prepared as a solution, suspension, emulsion, or syrup, being supplied either in liquid form or a dried form suitable for hydration in water or normal saline. For parenteral administration, an injectable composition for parenteral administration will typically contain the triptolide analog in a suitable intravenous solution, such as sterile physiological salt solution.

Liquid compositions can be prepared by dissolving or dispersing the triptolide analog (about 0.5% to about 20%) and optional pharmaceutical adjuvants in a carrier, such as, for example, aqueous saline, aqueous dextrose, glycerol, or ethanol, to form a solution or suspension. The high water solubility of the compounds of the invention make them particularly advantageous for administering in aqueous solution, e.g. by intraperitoneal injection. Although aqueous solutions are preferred, compositions in accordance with the invention may also be formulated as a suspension in a lipid (e.g., a triglyceride, a phospholipid, or a polyethoxylated castor oil such as "CREMOPHOR EL™"), in a liposomal suspension, or in an aqueous emulsion.

The compound may also be administered by inhalation, in the form of aerosol particles, either solid or liquid, preferably of respirable size. Such particles are sufficiently small to pass through the mouth and larynx upon inhalation and into the bronchi and alveoli of the lungs. In general, particles ranging from about 1 to 10 microns in size, and preferably less than about 5 microns in size, are respirable. Liquid compositions for inhalation comprise the active agent dispersed in an aqueous carrier, such as sterile pyrogen free saline solution or sterile pyrogen free water. If desired, the composition may be mixed with a propellant to assist in spraying the composition and forming an aerosol.

Methods for preparing such dosage forms are known or will be apparent to those skilled in the art; for example, see *Remington's Pharmaceutical Sciences* (19th Ed., Williams & Wilkins, 1995). The composition to be administered will contain a quantity of the selected compound in a pharmaceutically effective amount for effecting immunosuppression in a subject.

VI. Immunomodulating and Antiinflammatory Treatment

The compositions of the present invention are useful in applications for which triptolide has proven effective, e.g. in immunosuppression therapy, as in treating an autoimmune disease, preventing transplantation rejection, or treating or preventing graft-versus-host disease (GVHD). Triptolide and the present analogs are also useful for treatment of other inflammatory conditions, such as traumatic inflammation, and in reducing male fertility.

Immunosuppressive activity of compounds in vivo can be evaluated by the use of established animal models known in the art. Such assays may be used to evaluate the relative effectiveness of immunosuppressive compounds and to estimate appropriate dosages for immunosuppressive treatment. These assays include, for example, a well-characterized rat model system for allografts, described by Ono and Lindsey (1969), in which a transplanted heart is attached to the abdominal great vessels of an allogeneic recipient animal, and the viability of the transplanted heart is gauged by the heart's ability to beat in the recipient animal. A xenograft model, in which the recipient animals are of a different species, is described by Wang (1991) and Murase (1993). A model for evaluating effectiveness against GVHD involves injection of normal $F_1$ mice with parental spleen cells; the mice develop a GVHD syndrome characterized by splenomegaly and immunosuppression (Komgold, 1978; Gleichmann, 1984). Single cell suspensions are prepared from individual spleens, and microwell cultures are established in the presence and absence of concanavalin A to assess the extent of mitogenic responsiveness.

The method is useful for inhibiting rejection of a solid organ transplant, tissue graft, or cellular transplant from an incompatible human donor, thus prolonging survival and function of the transplant, and survival of the recipient. This use would include, but not be limited to, solid organ transplants (such as heart, kidney and liver), tissue grafts (such as skin, intestine, pancreas, gonad, bone, and cartilage), and cellular transplants (such as cells from pancreas, brain and nervous tissue, muscle, skin, bone, cartilage and liver).

The method is also useful for inhibiting xenograft (interspecies) rejection; i.e. in preventing the rejection of a solid organ transplant, tissue graft, or cellular transplant from a non-human animal, whether natural in constitution or bioengineered (genetically manipulated) to express human genes, RNA, proteins, peptides or other non-native, xenogeneic molecules, or bioengineered to lack expression of the animal's natural genes, RNA, proteins, peptides or other normally expressed molecules. The invention also includes the use of a composition as described above to prolong the survival of such a solid organ transplant, tissue graft, or cellular transplant from a non-human animal.

In another aspect, the invention includes a method of treatment or prevention of graft-versus-host disease, resulting from transplantation into a recipient of matched or mismatched bone marrow, spleen cells, fetal tissue, cord blood, or mobilized or otherwise harvested stem cells. The dose is preferably in the range 0.25–2 mg/kg body weight/day, preferably 0.5–1 mg/kg/day, given orally or parenterally.

Also included are methods of treatment of autoimmune diseases or diseases having autoimmune manifestations, such as Addison's disease, autoimmune hemolytic anemia, autoimmune thyroiditis, Crohn's disease, diabetes (Type I), Graves' disease, Guillain-Barre syndrome, systemic lupus erythematosus (SLE), lupus nephritis, multiple sclerosis, myasthenia gravis, psoriasis, primary biliary cirrhosis, rheumatoid arthritis and uveitis, asthma, atherosclerosis, Type I diabetes, psoriasis, and various allergies. In treating an autoimmune condition, the patient is given the composition on a periodic basis, e.g., 1–2 times per week, at a dosage level sufficient to reduce symptoms and improve patient comfort. For treating rheumatoid arthritis, in particular, the composition may be administered by intravenous injection or by direct injection into the affected joint. The patient may be treated at repeated intervals of at least 24 hours, over a several week period, or longer, following the onset of symptoms of the disease in the patient. For extended treatment, oral administration is typically preferred.

For therapy in transplantation rejection, the method is intended particularly for the treatment of rejection of heart, kidney, liver, cellular, and bone marrow transplants, and may also be used in the treatment of GVHD. The treatment is typically initiated perioperatively, either soon before or soon after the surgical transplantation procedure, and is continued on a daily dosing regimen, for a period of at least several weeks, for treatment of acute transplantation rejection. During the treatment period, the patient may be tested periodically for immunosuppression level, e.g., by a mixed lymphocyte reaction involving allogenic lymphocytes, or by taking a biopsy of the transplanted tissue.

In addition, the composition may be administered chronically to prevent graft rejection, or in treating acute episodes of late graft rejection. As above, the dose administered is preferably 1–25 mg/kg patient body weight per day, with lower amounts being preferred for parenteral administration, and higher amounts for oral administration. The dose may be increased or decreased appropriately, depending on the response of the patient, and over the period of treatment, the ability of the patient to resist infection.

The compounds are also useful as potentiators when administered concurrently with another immunosuppressive drug for immunosuppressive treatments as discussed above. A conventional immunosuppressant drug, such as cyclosporin A, FK506, azathioprine, rapamycin, mycophenolic acid, or a glucocorticoid, may thus be administered in an amount substantially less (e.g. 20% to 50% of the standard dose) than when the compound is administered alone. Alternatively, the triptolide analog and immunosuppressive drug are administered in amounts such that the resultant immunosuppression is greater than what would be expected or obtained from the sum of the effects obtained with the drug and triptolide analog used alone. Typically, the immunosuppressive drug and potentiator are administered at regular intervals over a time period of at least 2 weeks.

The compositions and method of the invention are also useful for the treatment of inflammatory conditions such as asthma, both intrinsic and extrinsic manifestations. For treatment of asthma, the composition is preferably administered via inhalation, but any conventional route of administration may be useful. The composition and method may also be used for treatment of other inflammatory conditions, including traumatic inflammation, inflammation in Lyme disease, psoriasis, chronic bronchitis (chronic infective lung disease), chronic sinusitis, sepsis associated acute respiratory distress syndrome, Behcet's disease, pulmonary sarcoidosis, pemphigus, pemphigoid inflammatory bowel disease, and ulcerative colitis.

The compositions of the invention may also be administered in combination with a conventional anti-inflammatory drug (or drugs), where the drug or amount of drug administered is, by itself, ineffective to induce the appropriate suppression or inhibition of inflammation.

The dose that is administered is preferably in the range of 1–25 mg/kg patient body weight per day, with lower amounts being preferred for parenteral administration, and higher amounts being preferred for oral administration. Optimum dosages can be determined by routine experimentation according to methods known in the art.

VII. Anticancer Treatment

Triptolide prodrugs have shown effectiveness in cancer treatment. See, for example, copending and co-owned U.S. application Ser. No. 09/766,156, which describes high efficacy of a triptolide prodrug, in comparison to 5-FU and CPT-11, in studies with tumor xenografts of the HT-29 human colon cancer cell line. The triptolide prodrug (a 14-succinate derivative of triptolide) strongly inhibited tumor growth, to a significantly greater degree than 5-FU and CPT-11, and induced tumor regression.

The invention thus includes the use of compositions as described above to treat cancers, including cancers involving cells derived from reproductive tissue (such as Sertoli cells, germ cells, developing or more mature spermatogonia, spermatids or spermatocytes and nurse cells, germ cells and other cells of the ovary), the lymphoid or immune systems (such as Hodgkin's disease and non-Hodgkin's lymphomas), the hematopoietic system, and epithelium (such as skin and gastrointestinal tract), solid organs, the nervous system, and musculo-skeletal tissue. The triptolide prodrugs may be used for treatment of various cancer cell types, including, but not limited to, breast, colon, small cell lung, large cell lung, prostate, malignant melanoma, liver, kidney, pancreatic, esophogeal, stomach, ovarian, cervical or lymphoma tumors. Treatment of breast, colon, lung, and prostate tumors is particularly contemplated. Treatment of leukemias is also contemplated. The composition may be administered to a patient afflicted with cancer and/or leukemia by any conventional route of administration, as discussed above.

The method is useful to slow the growth of tumors, prevent tumor growth, induce partial regression of tumors, and induce complete regression of tumors, to the point of complete disappearance. The method is also useful in preventing the outgrowth of metastases derived from solid tumors.

The compositions of the invention may be administered as sole therapy or with other supportive or therapeutic treatments not designed to have anti-cancer effects in the subject. The method also includes administering the invention compositions in combination with one or more conventional anti-cancer drugs or biologic protein agents, where the amount of drug(s) or agent(s) is, by itself, ineffective to induce the appropriate suppression of cancer growth, in an amount effective to have the desired anti-cancer effects in the subject. Such anti-cancer drugs include actinomycin D, camptothecin, carboplatin, cisplatin, cyclophosphamide, cytosine arabinoside, daunorubicin, doxorubicin, etoposide, fludarabine, 5-fluorouracil, hydroxyurea, gemcitabine, irinotecan, methotrexate, mitomycin C, mitoxantrone, paclitaxel, taxotere, teniposide, topotecan, vinblastine, vincristine, vindesine, and vinorelbine. Anti-cancer biologic protein agents include tumor necrosis factor (TNF), TNF-related apoptosis inducing ligand (TRAIL), other TNF-related or TRAIL-related ligands and factors, interferon, interleukin-2, other interleukins, other cytokines, chemokines, and factors, antibodies to tumor-related molecules or receptors (such as anti-HER2 antibody), and agents that react with or bind to these agents (such as members of the TNF super family of receptors, other receptors, receptor antagonists, and antibodies with specificity for these agents).

EXAMPLES

The following examples illustrate but are not intended in any way to limit the invention.

General Procedure for Esterification of Triptolide with Protected Amino Acids

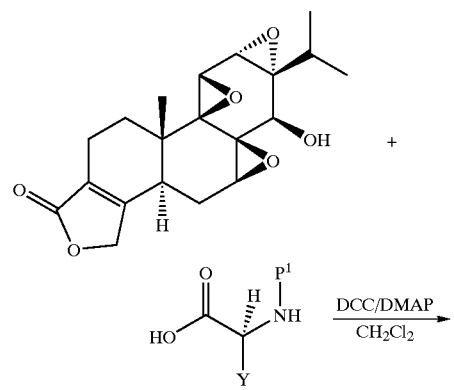

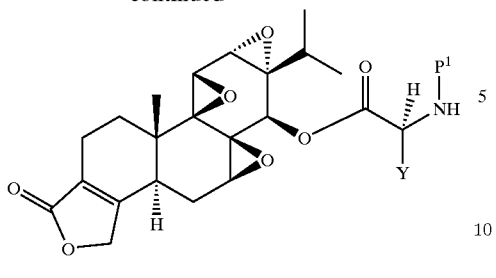

Protected amino acid (1.0 mmol, 5 eq) in dichloromethane (2 ml) is treated under nitrogen with 1,3-dicyclohexylcarbodiimide (DCC) (2.0 mmol, 10 eq) at room temperature for two hours. A solution of triptolide (0.2 mmol, 1 eq) and 4-dimethylaminopyridine (DMAP) (2.2 mmol, 11 eq) in dichloromethane (2 ml) is then added. The reaction mixture is stirred under nitrogen overnight. After the removal of the precipitate by filtration, the crude product is purified by preparative TLC. An α-amino acid is depicted above; β- and higher amino acids can also be used, as shown in the Examples below. Similar reactions could also be carried out with protected oligopeptides having a free carboxy terminus.

Example 1

Synthesis of Triptolide 14-N-t-Butoxycarbonyl-α-t-butyl-L-glutamate Ester (PG658)

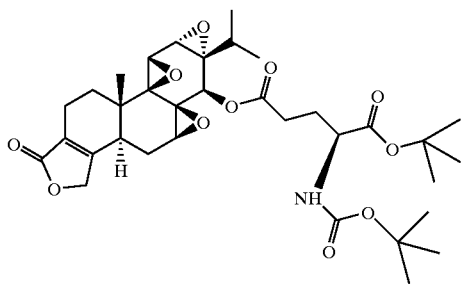

Using the above General Procedure, the product is obtained in 92% yield from N-tert-butoxycarbonyl-α-tert-butyl-L-glutamic acid and triptolide.

Analytical TLC Rf=0.59 (ethyl acetate/hexanes/methanol 1:1:0.1). IR (KBr): 3387.1, 2983.6, 2937.1, 2882.8, 1750.0, 1509.5, 1462.9, 1377.6, 1160.3, 1028.4, 873.3, 780.2, 562.9 cm$^{31\ 1}$. H$^1$NMR (300 MHz, CDCl$_3$): 5.17 (1H, d, NH), 5.08 (1H, d, 14-CH), 4.68 (2H, s, 19-CH$_2$), 4.16 (1H, m, NCH), 3.83 (1H, d, 11-CH), 3.54 (1 H, d, 12-CH), 3.47 (1H, d, 7-CH), 2.23 (3H, m, 5-CH and CH$_2$), 2.43 [2H, m, CH$_2$ (next to NCH)], 2.18 (2H, m, 6-CHβ and 2-CHβ), 2.00 (1H, m, 2-CHα), 1.90 (2H, m, 6-CHα and 15-CH), 1.58 (1H, m, 1-CHβ), 1.47 (9H, s, t-Bu), 1.44 (9H, s, t-Bu), 1.22 (1H, m, 1-CHα), 1.06 (3H, s, 20-CH$_3$), 0.96 (3H, d, 17-CH$_3$), 0.84 (3H, d, 16-CH$_3$) ppm.

Example 2

Synthesis of Triptolide 14-α-Benzyl-N-benzyloxycarbonyl-D-glutamate Ester (PG660)

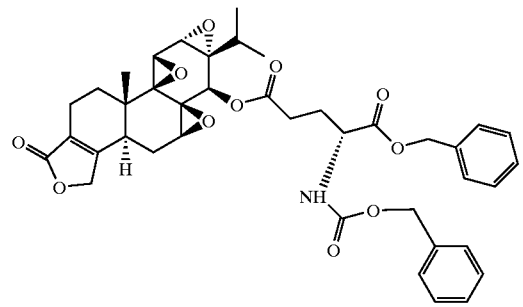

Using the above General Procedure, the product is obtained in 57% yield from α-benzyl-N-benzyloxycarbonyl-D-glutamic acid and triptolide.

Analytical TLC Rf=0.50 (ethyl acetate/hexanes/methanol 1:1:0.1). IR (KBr): 3376.8, 2973.5, 2944.2, 1749.1, 1683.1, 1529.1, 1463.1, 1265.2, 1221.2, 1177.2, 1030.5, 759.3, 207.9 cm$^{-1}$. H$^1$NMR (300 MHz, CDCl$_3$): 7.35 (10H, m, 2Ph), 5.53 (1H, d, NH), 5.18 (2H, s, CH$_2$Ar), 5.10 (2H, s, CH$_2$Ar), 5.06 (1H, d, 14-CH), 4.66 (2H, s, 19-CH$_2$), 4.49 (1H, m, NCH), 3.80 (1H, d, 11-CH), 3.49 (1H, d, 12-CH), 3.44 (1H, d, 7-CH), 2.66 (1H, m, 5-CH), 2.52 (2H, t, CH$_2$), 2.31 [2H, m, CH$_2$ (next to NCH)], 2.13 (2 H, m, 6-CHβ and 2-CHβ), 2.02 (1H, m, 2-CHα), 1.85 (2H, m, 6-CHα and 15-CH), 1.54 (1H, dd, 1-CHβ), 1.20 (1H, m, 1-CHα), 1.00 (3H, s, 20-CH$_3$), 0.93 (3H, d, 17-CH$_3$), 0.80 (3H, d, 16-CH3).

Example 3

Synthesis of Triptolide 14-γ-Benzyl-N-benzyloxycarbonyl-(L)-glutamate Ester, mixture with D-isomer (PG657)

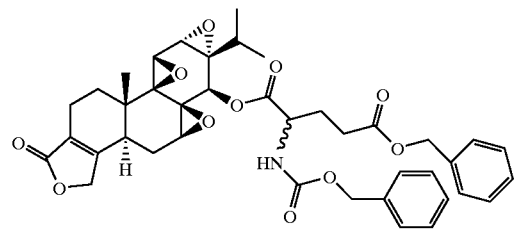

Using the above General Procedure, the title compounds are obtained as a diastereomeric mixture in 49% yield from γ-benzyl-N-benzyloxycarbonyl-L-glutamic acid and triptolide. Partial racemization of the L-amino acid occurs during the reaction.

Analytical TLC Rf=0.49 (ethyl acetate/hexanes/methanol 1:1:0.1). IR (KBr): 3368.4, 3038.6, 2975.4, 2940.4, 2884.2, 1761.4, 1529.9, 1452.6, 1178.9, 1031.6, 757.9, 708.8 cm$^1$. H$^1$NMR (300 MHz, CDCl$_3$): 7.34–7.07 (10H, m, 2Ph), 5.60–5.30 (1H, m, NH), 5.10–4.94 (5H, m, 2CH$_2$Ar and 14-CH), 4.71–4.46 (3H, m, 19-CH$_2$ and NCH), 3.80–3.79 (1H, m, aliphatic), 3.53–3.44 (2H, m, aliphatic), 2.65–0.74 (21H, m, aliphatic).

Example 4

Synthesis of 14-β-Benzyl-N-benzyloxycarbonyl-(L)-aspartate Triptolide Ester, mixture with D-isomer (PG659)

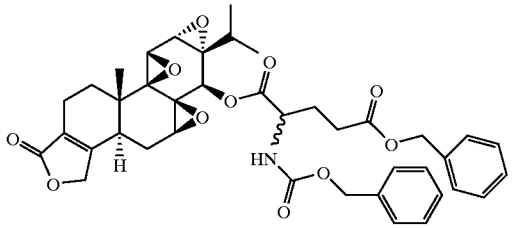

Using the above General Procedure, the title compounds are obtained as a diastereomeric mixture in 89% yield from β-benzyl-N-benzyloxycarbonyl-L-aspartic acid and triptolide. Partial racemization of the L-amino acid occurs during the reaction.

Analytical TLC Rf=0.50 (ethyl acetate\hexanes/methanol 1:1:0.1). IR (KBr): 3380.9, 3038.6, 2977.2, 2943.6, 2883.0, 1759.3, 1510.3, 1355.5, 1207.5, 1180.6, 1032.5, 992.1, 756.6, 702.8 cm$^{-1}$. H$^1$NMR (300 MHz, CDCl$_3$): 7.35–7.33 (10H, m, 2Ph), 5.91–5.79 (1H, m, NH), 5.21–5.03 (5H, m, 2CH$_2$Ar and 14-CH), 4.81–4.60 (3H, m, 19-CH$_2$ and 14-CH), 3.81–3.73 (10H, m aliphatic), 3.53–3.44 (2H, m, aliphatic), 3.24–2.94 (2H, m, aliphatic), 2.69–2.65 (1H, m, aliphatic), 2.34–0.69 (16H, m, aliphatic).

Example 5

Synthesis of Triptolide 14-N-tert-Butoxycarbonl-β-tert-butyl-(L)-aspartate Ester, mixture with D-isomer (PG664)

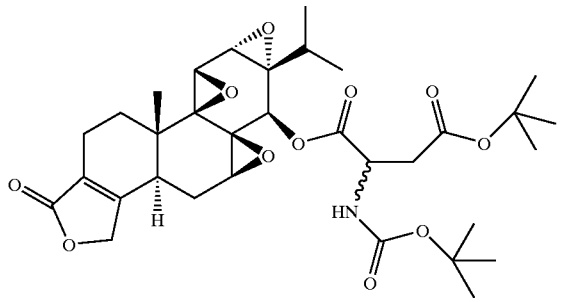

Using the above General Procedure, the title compounds are obtained as a diastereomeric mixture in 81% yield from β-benzyl-N-benzyloxycarbonyl-L-aspartic acid and triptolide. Partial racemization of the L-amino acid occurs during the reaction.

Analytical TLC Rf=0.63 (ethyl acetate/hexanes/methanol 1:1:0.1). H$^1$NMR (300 MHz, CDCl$_3$): 5.62–5.49 (1H, m, NH), 5.08–5.05 (1H, m, 14-CH), 4.74–4.57 (3 H, m, 19-CH$_2$ and NCH), 3.83–3.75 (1H, m, aliphatic), 3.55–3.45 (2H, m, aliphatic), 3.05–2.80 (2H, m, aliphatic), 2.70–2.66 (1H, m, aliphatic), 2.35–0.62 (34H, m, aliphatic).

Example 6

Synthesis of 14-γ-L-glutamate Ester of Triptolide (PG661)

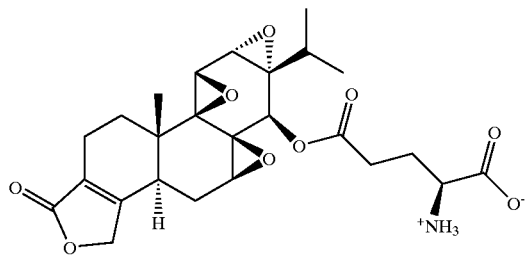

14-N-tert-butoxycarbonyl-α-tert-butyl-L-glutamate ester of triptolide (PG 658) (24.2 mg) is treated with trifluoroacetic acid (1 ml) at room temperature overnight. After removal of trifluoroacetic acid under vacuum, the crude product is purified by preparative TLC (isopropanol:aqueous ammonia 7:3) to give 8.2 mg of title compound.

Analygtical TLC Rf=0.65 (propan-1-ol/aqueous ammonia 7:3) H$^1$NMR (300 MHz, C$_5$D$_5$N): 6.26 (1H, s, 14-CH), 4.89 (2H, q, 19-CH), 4.66 (1H, d, 7-CH), 4.58 (1H, d, 11-CH), 4.45 (1H, m, NCH), 4.36 (1H, d, 12-CH), 3.62 (3H, S, NH$_3^+$), 2.73 (4H, m, COCH$_2$CH$_2$), 2.45 (2H, m, 6-CHβ and 15-CH), 2.06 (1H, m, 2-CHα), 1.66 (1H, m, 2-CHα), 1.54 (3H, s, 20-CH$_3$), 1.30 (3H, m, 6-CHα and 1-CH$_2$), 1.07 (3H, d, 17-CH$_3$), 0.93 (3H, d, 16-CH$_3$). HRMS (FAB) m/z calcd for C$_{25}$H$_{32}$NO$_9^+$ (MH$^+$) 490.2077, found 490.2065.

Example 7

Apoptosis Assays

A. Incubation of Compounds with Human Serum.

Pooled human serum was stored in aliquots at −80° C. Test compounds were added at 20 mM to thawed human serum in 1.5 ml microfuge tubes and incubated at 37° C. in a water bath for 48 hours. The test samples were placed on ice until dilution for the bioassay. Controls consisted of the compounds incubated in complete tissue culture medium (RPMI 1640 medium plus 5% heat-inactivated fetal calf serum, 1% HEPES, 1% pen/strep, 1% glutamine) rather than human serum.

B. Terminal Deoxynucleotidyl Transferase Apoptosis Assay.

Test samples were diluted to 1 mM in complete tissue culture medium. Aliquots were placed in microculture plates and serial dilutions were prepared so that the final concentration would encompass the range of 2 to 6,000 nM with half-log increments. Cells from an exponentially expanding culture of the Jurkat human T lymphocyte cell line (#TIB-152 obtained from American Type Culture Collection, Manassas, Va.) were harvested, washed once by centrifugation and dilution in complete tissue culture medium, and diluted to a concentration of 1×10$^6$ cells/ml. A volume of 100 μl of Jurkat cells (1×10$^5$ cells) was added to wells containing 100 μl of the diluted compounds, and the plates were incubated at 37° C. in a 5% CO$_2$ incubator. After 24 hours, the plates were centrifuged to pellet the cells, and the cells were washed with PBS. The cells were fixed in paraformaldehyde, washed, treated with ethanol, washed and then incubated with the enzyme terminal deoxynucleotidyl transferase (TdT) and fluorescein labeled-deoxyuridine (dUTP). The process allows 3' end labeling of DNA molecules which were nicked during the DNA fragmentation phase of apoptosis (terminal deoxynucleotidyl transferase dUTP nick end labeling; TUNEL labeling). The cells were washed, treated with ribonuclease, washed and resuspended in medium containing propidium iodide to distinguish intact apoptotic cells. The contents of the assay wells were individually transferred into test tubes, and apoptosis was analyzed using a FACSCalibur flow cytometer (BD Immunocytometry Systems, San Jose, Calif.). Cells positive for Fl-dUTP were considered to be apoptotic, and the data were calculated as percent apoptotic cells.

C. Annexin V Apoptosis Assay

Test samples (incubated in human serum as described in section A) were prepared and diluted as described in section B, and Jurkat human T lymphocyte cells were prepared and added to wells containing 100 μl of the diluted compounds, also as described in section B. The plates were incubated at 37° C. in a 5% $CO_2$ incubator. After 24 hours, the plates were centrifuged to pellet the cells, and the cells were washed twice with 2% heat-inactivated fetal calf serum in PBS. To each well, 500 ul of binding buffer was added, according to the Annexin V assay procedure (BioVision, Inc., Mountain View, Calif.). Next, 5 μl of the fluorescein isothiocyanate (FITC) conjugate of Annexin V (BioVision, Inc.) was added to each well, followed by 5 minutes of incubation in the dark. In some assays, propidium iodide (BioVision, Inc.) was added at this stage to check for necrotic cells. The contents of the wells were individually transferred into test tubes, and apoptosis was analyzed using a FACSCalibur flow cytometer (BD Immunocytometry Systems, San Jose, Calif.). Cells positive for Annexin V binding were considered to be apoptotic, and the data were calculated as percent apoptotic cells.

For the assays in sections B and C, data were plotted as the concentration of compound incubated in serum versus percent apoptotic cells, and the concentration of compound inducing 50% apoptosis (ED50) was calculated from these dose response curves. The percent conversion of the test compounds to bioactive compound (assumed to be triptolide) was calculated in reference to the result with triptolide incubated in parallel in human serum in the same experiment, as the percent of the ED50 of the compound compared to that for triptolide, which was taken as 100%.

Example 8

IL-2 Production Assay

Test samples, incubated in human serum as described in Example 7A, were diluted to 1 mM in complete tissue culture medium. Aliquots were placed in microculture plates that had been coated with anti-CD3 antibody (used to stimulate the production of IL-2 by Jurkat cells), and serial dilutions were prepared so that the final concentration would encompass the range of 0.001 to 10,000 nM in log increments. Cells from an exponentially expanding culture of the Jurkat human T lymphocyte cell line (#TIB-152 obtained from American Type Culture Collection, Manassas, Va.) were harvested, washed once by centrifugation and dilution in complete tissue culture medium, and diluted to a concentration of 2×10⁶ cells/ml. A volume of 50 μl of Jurkat cells (1×10⁵ cells) was added to wells containing 100 μl of the diluted compounds, 50 μl of PMA (10 ng/ml) was added to each well, and the plates were incubated at 37° C. in a 5% $CO_2$ incubator. After 24 hours, the plates were centrifuged to pellet the cells, 150 μl of supernatant was removed from each well, and the samples were stored at −20° C. The stored supernatants were analyzed for human IL-2 concentration using the Luminex 100 (Luminex Corporation, Austin, Tex.), Luminex microspheres coupled with anti-IL-2 capture antibody, and fluorochrome-coupled anti-IL-2 detection antibody. The data were expressed as ng/ml of IL-2.

The data were plotted as the concentration of compound incubated in serum versus IL-2 concentration. The concentration of compound inducing a 50% decrease in the IL-2 concentration (IC50) was calculated from these dose response curves. The percent conversion of the test compound to bioactive compound (assumed to be triptolide) was calculated in reference to the result with triptolide incubated in parallel in human plasma in the same experiment, as the percent of the IC50 of the compound compared to that for triptolide, which was taken as 100%.

While the invention has been described with reference to specific methods and embodiments, it will be appreciated that various modifications may be made without departing from the invention.

It is claimed:

1. A compound having the structure:

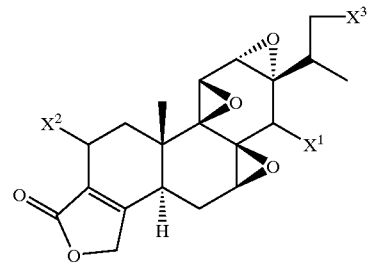

wherein $X^1$ is OH or $OR^1$ and $X^2$ and $X^3$ are independently OH, $OR^1$, or H, with the proviso that at least one of $X^1$, $X^2$ and $X^3$ is $OR^1$, and at least one of $X^2$ and $X^3$ is H; and $R^1$ is selected from the group consisting of:

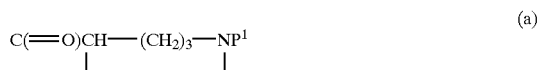
(a)

(b):

(c)

(d)

and

(e):

wherein:

Y is a side chain of a naturally occurring amino acid or a one- or two-carbon homolog thereof;

P¹ is selected from the group consisting of H, C(=O)OR², and C(=O)R³, wherein each of R² and R³ is independently H, alkyl, alkenyl, aryl, or aralkyl;

m is an integer from 0–5;

n is an integer from 0–5;

z is an integer from 2–10;

and

P² is selected from the group consisting of H, alkyl, alkenyl, aryl, or aralkyl.

2. A compound as recited in claim 1, wherein the chiral α-carbon bearing the nitrogen atom, in each of groups (a)–(d), is of the L configuration.

3. A compound as recited in claim 1, wherein the chiral α-carbon bearing the nitrogen atom, in each of groups (a)–(d), is of the D configuration.

4. The compound in claim 1, wherein Y is a side chain of a naturally occurring amino acid.

5. A compound as recited in claim 1, wherein $X^2=X^3=H$.

6. A compound as recited in claim 5, wherein $R^1$ is selected from

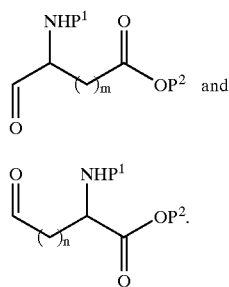 and (c)

(d)

7. A compound as recited in claim 6, wherein $R^1$, is

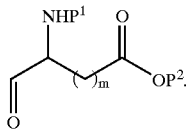

(c)

8. A compound as recited in claim 1, wherein P¹ and P² are both non-hydrogen.

9. A compound as recited in claim 8, wherein R² and R³ are both non-hydrogen.

10. A method of anticancer treatment, directed to the colon, breast, lung, or prostate, comprising administering to a subject in need of such treatment, in a pharmaceutically acceptable vehicle, a therapeutically effective amount of a compound in accordance with claim 1 or a pharmaceutically acceptable salt thereof.

11. The method of claim 10, wherein said treatment is inhibition of tumor growth.

12. A method of effecting immunosuppression, comprising administering to a subject in need of such treatment, a therapeutically effective amount of a compound in accordance with claim 1 or a pharmaceutically acceptable salt thereof, in a pharmaceutically acceptable vehicle.

13. The method of claim 12, wherein said immunosuppression comprises inhibition of transplant rejection.

14. The method of claim 12, wherein said immunosuppression comprises inhibition of graft-versus-host disease.

15. The method of claim 12, wherein said immunosuppression comprises treatment of an autoimmune disease.

* * * * *